United States Patent
Fecant et al.

(10) Patent No.: US 11,806,695 B2
(45) Date of Patent: Nov. 7, 2023

(54) METHOD FOR THE PHOTOCATALYTIC REDUCTION OF CO₂ USING A MICROPOROUS CRYSTALLINE METAL SULFIDE PHOTOCATALYST

(71) Applicant: IFP Energies Nouvelles, Rueil-Malmaison (FR)

(72) Inventors: Antoine Fecant, Rueil-Malmaison (FR); Raquel Martinez Franco, Rueil-Malmaison (FR); Gerhard Pirngruber, Rueil-Malmaison (FR); Philibert Leflaive, Rueil-Malmaison (FR)

(73) Assignee: IFP Energies Nouvelles, Rueil-Malmaison (FR)

( * ) Notice: Subject to any disclaimer, the term of this patent is extended or adjusted under 35 U.S.C. 154(b) by 49 days.

(21) Appl. No.: 17/622,886

(22) PCT Filed: Jun. 16, 2020

(86) PCT No.: PCT/EP2020/066568
§ 371 (c)(1),
(2) Date: Dec. 27, 2021

(87) PCT Pub. No.: WO2020/260064
PCT Pub. Date: Dec. 30, 2020

(65) Prior Publication Data
US 2022/0226802 A1 Jul. 21, 2022

(30) Foreign Application Priority Data
Jun. 28, 2019 (FR) ........................... 1907102

(51) Int. Cl.
*B01J 27/04* (2006.01)
*C01B 32/40* (2017.01)
*B01D 53/00* (2006.01)
*B01D 53/86* (2006.01)
*B01J 31/02* (2006.01)
*B01J 35/00* (2006.01)
*C07C 1/02* (2006.01)

(52) U.S. Cl.
CPC ............ *B01J 27/04* (2013.01); *B01D 53/007* (2013.01); *B01D 53/8671* (2013.01); *B01J 31/0237* (2013.01); *B01J 35/004* (2013.01); *C01B 32/40* (2017.08); *C07C 1/02* (2013.01); *B01D 2255/2094* (2013.01); *B01D 2255/20792* (2013.01); *B01D 2255/802* (2013.01); *B01D 2255/9205* (2013.01); *B01D 2257/504* (2013.01); *C07C 2523/06* (2013.01); *C07C 2523/14* (2013.01); *C07C 2527/04* (2013.01); *C07C 2531/02* (2013.01)

(58) Field of Classification Search
None
See application file for complete search history.

(56) References Cited

U.S. PATENT DOCUMENTS

| | | | |
|---|---|---|---|
| 2002/0098977 A1* | 7/2002 | Park | B01J 29/06 502/349 |
| 2013/0252798 A1 | 9/2013 | Ling et al. | |

FOREIGN PATENT DOCUMENTS

| | | | | |
|---|---|---|---|---|
| CN | 104667979 A | * | 6/2015 | ........... B01J 35/0006 |
| CN | 106006717 A | | 10/2016 | |
| CN | 109046385 A | | 12/2018 | |
| CN | 109225273 A | | 1/2019 | |
| CN | 109331883 A | | 2/2019 | |
| FR | 3026965 A1 | * | 4/2016 | ........... B01J 35/0006 |

OTHER PUBLICATIONS

CN-104667979-A, English translation (Year: 2015).*
FR-3026965-A1, English translation (Year: 2016).*
International Search Report dated Aug. 12, 2020 issued in corresponding PCT/EP2020/066568 application (3 pages).

* cited by examiner

*Primary Examiner* — Stefanie J Cohen
(74) *Attorney, Agent, or Firm* — MILLEN WHITE ZELANO & BRANIGAN, PC; Brion P. Heaney

(57) ABSTRACT

The invention describes a process for the photocatalytic reduction of carbon dioxide carried out in the liquid phase and/or in the gas phase under irradiation employing a photocatalyst of microporous crystalline metal sulfide type, said process being carried out by bringing a charge containing the $CO_2$ and at least one sacrificial compound into contact with said photocatalyst, then by irradiating the photocatalyst by at least one irradiation source producing at least one wavelength lower than the bandgap width of said photocatalyst, so as to reduce the $CO_2$ and to oxidize the sacrificial compound, so as to produce an effluent containing, at least in part, $C_1$ or more carbon-based molecules other than $CO_2$.

16 Claims, No Drawings

METHOD FOR THE PHOTOCATALYTIC REDUCTION OF CO₂ USING A MICROPOROUS CRYSTALLINE METAL SULFIDE PHOTOCATALYST

TECHNICAL FIELD

The field of the invention is that of the photocatalytic reduction of carbon dioxide ($CO_2$) under irradiation by the use of a photocatalyst.

STATE OF THE ART

Fossil fuels, such as coal, oil and natural gas, are the main conventional energy sources in the world due to their availability, stability and high energy density. However, the combustion produces carbon dioxide emissions which are considered to be the main cause of global warming. Thus, there is a growing need to reduce $CO_2$ emissions, either by capturing said $CO_2$ or by converting it.

Although "passive" carbon capture and sequestration (CCS) is generally considered to be an effective process for reducing $CO_2$ emissions, other strategies have to be envisaged, in particular "active" strategies for the conversion of $CO_2$ into products having an economic value, such as fuels and industrial chemicals.

Such "active" strategies are based on the reduction of carbon dioxide to give upgradable products. The reduction of carbon dioxide can be carried out biologically, thermally, electrochemically or also photocatalytically. Among these options, the photocatalytic reduction of $CO_2$ is gaining increased attention since it can potentially consume alternative energy forms, for example by harnessing solar energy, which is abundant, inexpensive, and environmentally clean and safe.

The photocatalytic reduction of carbon dioxide makes it possible to obtain $C_1$ or more carbon-based molecules, such as carbon monoxide (CO), methane, methanol, ethanol, formaldehyde, formic acid or also other molecules, such as carboxylic acids, aldehydes, ketones or various alcohols. These molecules can have an energy usefulness directly, such as methanol, ethanol, formic acid or also methane and all the $C_1^+$ hydrocarbons. Carbon monoxide (CO) can also be upgraded in terms of energy as a mixture with molecular hydrogen for the formation of fuels by the Fischer-Tropsch synthesis. The molecules of carboxylic acids, aldehydes, ketones or various alcohols can, for their part, find applications in chemical or petrochemical processes. All these molecules are thus of great interest from an industrial viewpoint.

Photocatalysis is based on the principle of activation of a semiconductor or of a set of semiconductors, such as a photocatalyst, using the energy provided by irradiation. Photocatalysis can be defined as the absorption of a photon, the energy of which is greater than the bandgap width between the valence band and the conduction band, which induces the formation of an electron-hole pair in the case of a semiconductor. There is thus excitation of an electron to the conduction band and formation of a hole on the valence band. This electron-hole pair will make possible the formation of free radicals which will either react with compounds present in the medium, in order to initiate oxidation/reduction reactions, or else recombine according to various mechanisms. A semiconductor is characterized by its bandgap, i.e. the energy difference between its conduction band and its valence band which is specific to it. Any photon with an energy greater than its bandgap can be absorbed by the semiconductor. No photon with an energy lower than its bandgap can be absorbed by the semiconductor.

Processes for the photocatalytic reduction of carbon dioxide in the presence of a sacrificial compound are known in the prior art.

Halmann et al. (Solar Energy, 31, 4, 429-431, 1983) evaluated the performance qualities of three semiconductors ($TiO_2$, $SrTiO_3$ and $CaTiO_3$) for the photocatalytic reduction of $CO_2$ in an aqueous medium. They observed the production of formaldehyde, formic acid and methanol.

Anpo et al. (J. Phys. Chem. B, 101, pp. 2632-2636, 1997) studied the photocatalytic reduction of $CO_2$ with water vapor over $TiO_2$-based photocatalysts anchored in zeolite micropores. These exhibited a very high selectivity for gaseous methanol.

Mori et al. (RSC Adv., 2012, 2 (8), 3165-3172) demonstrated the improvement in the photocatalytic activity of microporous or mesoporous crystalline materials based on titanium oxide compared with a bulk titanium dioxide for the reduction of $CO_2$.

Thus, while the use of microporous crystalline photocatalysts is known from the state of the art, said photocatalysts often exhibit high bandgap widths (>3 eV), thus making it possible to upgrade only a minimal portion of the photons of the solar spectrum.

It is known from the prior art to employ materials of the nonmicroporous (bulk) metal sulfide type as photocatalyst (O. Stroyuk et al., Chem. Soc. Rev., 2108, 47, p. 5354). This type of material has the advantage of exhibiting smaller bandgap widths (<3 eV) than most metal oxides, such as $TiO_2$, for example.

OBJECTS OF THE INVENTION

The object of the invention is to provide a new, durable and more efficient route for the production of upgradable carbon-based molecules by photocatalytic conversion of carbon dioxide employing a photocatalyst based on microporous crystalline metal sulfide. The process for the photocatalytic reduction of $CO_2$ according to the invention makes it possible to achieve improved performance qualities in comparison with the implementations known for this reaction. The photocatalytic reduction processes according to the prior art differ from the invention in that the microporous crystalline semiconductors exhibit high bandgap widths (>3 eV) which do not make it possible for the materials to absorb a large amount of photons resulting from the visible portion of the solar spectrum. This is because the photocatalytic reduction processes according to the prior art use photocatalysts based on metal sulfide not exhibiting microporosity. Without being committed to any theory, the presence of microporosity in the photocatalyst makes possible a short transit time of the reactive charges, electrons $e^-$ and holes $h^+$, and thus lower recombination rates.

More particularly, the invention describes a process for the photocatalytic reduction of carbon dioxide carried out in the liquid phase and/or in the gas phase, said process comprising the following stages:

a) a charge containing carbon dioxide and at least one sacrificial compound is brought into contact with a photocatalyst comprising at least one semiconductor based on microporous crystalline metal sulfide;

b) the photocatalyst is irradiated by at least one irradiation source producing at least one wavelength which is lower than the bandgap width of said photocatalyst, said stage b)

being carried out at a temperature of between −10° C. and 200° C. and at a pressure of between 0.01 MPa and 70 MPa.

Advantageously, said photocatalyst comprising at least one semiconductor is provided in the form of a solid exhibiting a chemical composition expressed on an anhydrous basis, in terms of moles, by the following general formula:

$$X_aY_bS_8:cR$$

where:
X represents at least one tetravalent element chosen from Sn, Ge, Ti or Zr,
Y represents at least one divalent metal chosen from Zn, Cd or Ni,
R represents at least one nitrogenous organic entity,
S is sulfur,
"a" is the molar amount of X of between 0.1 and 5;
"b" is the molar amount of Y of between 0.2 and 8;
"c" is the molar amount of the nitrogenous organic entity R of between 0 and 4.

Advantageously, said photocatalyst comprising at least one semiconductor is provided in the form of a solid exhibiting a chemical composition expressed on an anhydrous basis, in terms of moles, defined by the following general formula:

$$Sn_aZn_bS_8:cR$$

where:
R represents at least one nitrogenous organic entity;
S is sulfur;
"a" is the molar amount of Sn of between 0.1 and 5;
"b" is the molar amount of Zn of between 0.2 and 8;
"c" is the molar amount of the nitrogenous organic entity R of between 0 and 4.

Advantageously, "c" is between 0.2 and 4.
Advantageously, said solid exhibits an X-ray diffraction diagram including at least the lines listed in table 1 below:

| 2 theta (°) | $d_{hkl}$ (Å) | $I_{rel}$ |
|---|---|---|
| 7.95 | 11.11 | S |
| 8.88 | 9.95 | m |
| 10.18 | 8.68 | w |
| 11.10 | 7.97 | VS |
| 11.72 | 7.54 | S |
| 15.37 | 5.76 | m |
| 16.71 | 5.30 | w |
| 17.36 | 5.11 | w |
| 21.49 | 4.13 | m |
| 22.30 | 3.98 | m |
| 23.31 | 3.81 | w |
| 30.05 | 2.97 | w |
| 33.34 | 2.69 | w |
| 35.96 | 2.50 | w |
| 40.80 | 2.21 | w | where VS = very strong; S = strong; m = medium; w = weak.

Advantageously, R is an organic compound comprising at least two nitrogen atoms.
Advantageously, R is 1,3-bis(4-piperidinyl)propane.
Advantageously, said semiconductor has a micropore volume of between 0.01 and 0.50 cm³/g.
Advantageously, the width of the bandgap of said photocatalyst is between 1.24 and 3 eV.

In one embodiment according to the invention, when said process is carried out in the gas phase, the sacrificial compound is a gaseous compound chosen from water, ammonia, hydrogen, methane and an alcohol.

In one embodiment according to the invention, when the process is carried out in the liquid phase, the sacrificial compound is a soluble solid or liquid compound chosen from water, ammonia, an alcohol, an aldehyde or an amine.

Advantageously, the irradiation source is a natural irradiation source.

Preferably, the irradiation source emits at at least one wavelength range greater than 280 nm.

More preferentially, the irradiation source emits at at least one wavelength range of between 315 nm and 800 nm.

Definitions and Abbreviations

The term "sacrificial compound" corresponds to an oxidizable compound, in the gaseous or liquid form.

The term "$C_1$ or more ($C_{1+}$) carbon-based molecules" is understood to mean molecules resulting from the reduction of $CO_2$ containing one or more carbon atoms, with the exception of $CO_2$. Such molecules are, for example, CO, methane, methanol, ethanol, formaldehyde, formic acid, methane or also other molecules, such as carboxylic acids, aldehydes, ketones, various alcohols or hydrocarbons containing more than 2 carbon atoms.

The groups of chemical elements correspond to those of the CAS classification (CRC Handbook of Chemistry and Physics, published by CRC Press, editor D. R. Lide, 81st edition, 2000-2001). For example, group VIII according to the CAS classification corresponds to the metals of columns 8, 9 and 10 according to the new IUPAC classification.

The textural and structural properties of the support and of the catalyst described below are determined by the characterization methods known to a person skilled in the art.

The micropore volume and the pore distribution are determined by nitrogen porosimetry, as described in the work "Adsorption by Powders and Porous Solids. Principles, Methodology and Applications", written by F. Rouquérol, J. Rouquérol and K. Sing, Academic Press, 1999.

The term "specific surface" is understood to mean the BET specific surface ($S_{BET}$ in m²/g) determined by nitrogen adsorption in accordance with the standard ASTM D 3663-78 drawn up from the Brunauer-Emmett-Teller method described in the periodical *The Journal of the American Chemical Society*, 1938, 60, 309.

The maximum wavelength absorbable by a semiconductor is calculated using the following equation:

$$\lambda_{max} = \frac{h \times c}{E_g}$$

with $\lambda_{max}$ the maximum wavelength absorbable by a semiconductor (in m), h Planck's constant ($4.13433559 \times 10^{-15}$ eV·s), c the speed of light in vacuum (299 792 458 m·s⁻¹) and $E_g$ the bandgap width of the semiconductor (in eV).

The term "reaction medium" is understood to mean the mixture formed by the charge containing the carbon dioxide, the sacrificial compound and the photocatalyst.

In the present description, according to the IUPAC convention, the term "micropores" is understood to mean the pores, the diameter of which is less than 2 nm, that is to say 0.002 μm; "mesopores" the pores, the diameter of which is greater than 2 nm, that is to say 0.002 μm, and less than 50 nm, that is to say 0.05 μm, and "macropores" the pores, the diameter of which is greater than 50 nm, that is to say 0.05 μm.

DETAILED DESCRIPTION OF THE INVENTION

The invention describes a process for the photocatalytic reduction of carbon dioxide carried out in the liquid phase and/or in the gas phase, said process comprising the following stages:
a) a charge containing carbon dioxide and at least one sacrificial compound is brought into contact with a photocatalyst comprising at least one semiconductor based on microporous crystalline metal sulfide;
b) the photocatalyst is irradiated by at least one irradiation source producing at least one wavelength which is lower than the bandgap width of said photocatalyst, said stage b) being carried out at a temperature of between −10° C. and 200° C. and at a pressure of between 0.01 MPa and 70 MPa.

Stage a) of Bringing into Contact a Charge, at Least One Sacrificial Compound and a Photocatalyst Based on Microporous Crystalline Metal Sulfide, According to stage a) of the process according to the invention, a charge containing carbon dioxide ($CO_2$) and at least one sacrificial compound is brought into contact with a photocatalyst based on microporous crystalline metal sulfide.

The contacting operation can be carried out by any means known to a person skilled in the art. The contacting of the charge and of the photocatalyst can be carried out in a crossed fixed bed, in a sweeping fixed bed or in suspension (also called "slurry"). The photocatalyst can also be deposited directly on optical fibers.

When the contacting is in a crossed fixed bed, the photocatalyst is preferentially deposited as a layer on a porous support, for example of the ceramic or metallic sintered type, and the charge containing the carbon dioxide to be converted in gaseous and/or liquid form is sent through the photocatalytic bed.

When the contacting is in a sweeping fixed bed, the photocatalyst is preferentially deposited on a nonporous support of ceramic or metallic type, and the charge containing the carbon dioxide to be converted in gaseous and/or liquid form is sent over the photocatalytic bed.

When the contacting is in suspension, the photocatalyst is preferentially in the form of particles in suspension in a liquid or liquid/gas charge containing the carbon dioxide. In suspension, the process can be implemented in a closed reactor or continuously.

The Charge and the Sacrificial Compounds

The process is carried out in the gas or liquid phase or gas and liquid biphase, meaning respectively that the charge treated according to the process is provided in the gaseous, liquid or gaseous and liquid two-phase form. Preferably, the process is carried out in the gas phase.

When the process is carried out in the gas phase, with a charge provided in the gaseous form, the $CO_2$ present in the charge is also in the gaseous form, and the sacrificial compound(s) used for stage a) are also in the gaseous form.

The gaseous sacrificial compounds are oxidizable compounds, such as water ($H_2O$), ammonia ($NH_3$), molecular hydrogen ($H_2$), methane ($CH_4$) or also alcohols, or their mixture. Preferably, the gaseous sacrificial compounds are water or molecular hydrogen. A diluent fluid, such as $N_2$ or Ar, can be present in the reaction medium when the process is carried out in the gas phase. The presence of a diluent fluid is not required for carrying out the invention; however, it can be useful to add said diluent to the charge in order to ensure the dispersion of the charge and/or of the photocatalyst in the reaction medium, the control of the adsorption of the reactants/products at the surface of the photocatalyst, the control of the absorption of the photons by the photocatalyst, the dilution of the products in order to limit their recombination and other side reactions of the same order. The presence of a diluent fluid also makes it possible to control the temperature of the reaction medium, which can thus compensate for the possible exo/endothermicity of the photocatalyzed reaction. The nature of the diluent fluid is chosen so that its influence is neutral on the reaction medium or that its possible reaction does not harm the performing of the desired reduction of the carbon dioxide.

When the process is carried out in the liquid phase, with a charge provided in the liquid form, the latter can be in the ionic, organic or aqueous form. The charge in the liquid form is preferentially aqueous.

When the liquid charge is an aqueous solution, the $CO_2$ is then dissolved in the form of aqueous $CO_2$, of hydrogencarbonate or of carbonate. The sacrificial compounds used in this case are liquid or solid oxidizable compounds which are soluble in the liquid charge, such as water ($H_2O$), ammonia ($NH_3$), alcohols, aldehydes or amines. Preferably, the sacrificial compound is water. The pH is generally between 2 and 12, preferably between 3 and 10.

Optionally, and in order to modulate the pH of the aqueous liquid charge, a basic or acidic agent can be added to the charge. The basic agent can be chosen from alkali metal or alkaline earth metal hydroxides or organic bases, for example amines or ammonia. The acidic agent can be chosen from inorganic acids, for example nitric acid, sulfuric acid, phosphoric acid, hydrochloric acid or hydrobromic acid, or organic acids, such as carboxylic or sulfonic acids. Optionally, when the liquid charge is aqueous, the latter can contain, in any amount, any solvated ion, such as, for example, $K^+$, $Li^+$, $Na^+$, $Ca^{2+}$, $Mg^{2+}$, $SO_4^{2-}$, $Cl^-$, $F^-$ or $NO_3^{2-}$.

The Photocatalyst

The photocatalyst comprises, preferably consists of, one or more semiconductors based on microporous crystalline metal sulfide.

Preferably, said semiconductor is provided in the form of a solid comprising a chemical composition expressed on an anhydrous basis, in terms of moles, by the following general formula:

$$X_aY_bS_8\text{:}cR$$

where:
X represents at least one tetravalent element chosen from Sn, Ge, Ti or Zr,
Y represents at least one divalent metal chosen from Zn, Cd or Ni,
R represents at least one nitrogenous organic entity,
S is sulfur,
"a" is the molar amount of X of between 0.1 and 5;
"b" is the molar amount of Y of between 0.2 and 8;
"c" is the molar amount of the nitrogenous organic entity R of between 0 and 4.

More preferentially, said photocatalyst comprises a solid, called IZM-5, said solid IZM-5 exhibiting a chemical composition expressed on an anhydrous basis, in terms of moles, defined by the following general formula:

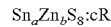

$$Sn_aZn_bS_8\text{:}cR$$

where:
R represents at least one nitrogenous organic entity;
S is sulfur;

"a" is the molar amount of Sn of between 0.1 and 5, preferably between 1 and 4;

"b" is the molar amount of Zn of between 0.2 and 8, preferably between 0.2 and 2;

"c" is the molar amount of the nitrogenous organic entity R of between 0 and 4, preferably between 0.5 and 3.

Preferably, R comprises two nitrogen atoms, and very preferentially R is 1,3-bis(4-piperidinyl)propane, the expanded formula of which is given below.

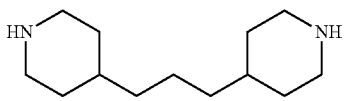 [SMILES: C(CC1CCNCC1)CC1CCNCC1]

The constituent semiconductor of said photocatalyst is crystalline and exhibits a very specific X-ray diffraction signal. More preferentially, the photocatalyst comprises the solid IZM-5 exhibiting an X-ray diffraction diagram including at least the lines listed in table 1 above.

The relative intensity $I_{rel}$ is given with respect to a relative intensity scale where a value of 100 is assigned to the most intense line of the X-ray diffraction diagram: 5≤w<10; 10≤m<15; 15≤S<50; VS≥50.

This diffraction diagram is obtained by radiocrystallographic analysis by means of a diffractometer using the conventional powder method with the K$\alpha_1$ radiation of copper ($\lambda$=1.5406 Å). On the basis of the position of the diffraction peaks represented by the angle 2θ, the lattice spacings $d_{hkl}$ characteristic of the sample are calculated using Bragg's law. The measurement error $\Delta(d_{hkl})$ over $d_{hkl}$ is calculated by means of Bragg's law as a function of the absolute error $\Delta(2\theta)$ assigned to the measurement of 2θ. An absolute error $\Delta(2\theta)$ equal to ±0.02° is commonly accepted. The relative intensity $I_{rel}$ assigned to each value of $d_{hkl}$ is measured according to the height of the corresponding diffraction peak. In the column of the $d_{hkl}$ values, the mean values of the lattice spacings have been shown in angstroms (Å). Each of these values must be assigned the measurement error $\Delta(d_{hkl})$ of between ±0.6 Å and ±0.01 Å.

The constituent semiconductor of said photocatalyst preferably exhibits a micropore volume of between 0.01 and 0.50 cm³/g, preferably between 0.05 and 0.30 cm³/g.

The bandgap width of said photocatalyst is preferably between 1.24 and 3 eV.

The photocatalyst can optionally be doped with one or more ions chosen from metal ions, such as, for example, V, Ni, Cr, Mo, Fe, Sn, Mn, Co, Re, Nb, Sb, La, Ce, Ta or Ti ions, nonmetal ions, such as, for example, C, N, S, F or P ions, or by a mixture of metal and nonmetal ions.

The photocatalyst can optionally contain particles comprising one or more element(s) in the metal state, chosen from an element from groups IVb, Vb, VIB, VIIb, VIIIb, Ib, IIb, IIIa, IVa and Va of the periodic table of the elements. Said particles comprising one or more element(s) in the metal state are in direct contact with said semiconductor. Said particles can be composed of a single element in the metal state or of several elements in the metal state which can form an alloy. The term "element in the metal state" (not to be confused with "metal element") is understood to mean an element belonging to the family of the metals, said element being at the zero oxidation state (and thus in the metal form). Preferably, the element(s) in the metal state are chosen from a metal element from groups VIIb, VIIIb, Ib and IIb of the periodic table of the elements, and in a particularly preferred way from platinum, palladium, gold, nickel, cobalt, ruthenium, silver, copper, rhenium or rhodium. Said particles comprising one or more element(s) in the metal state are preferentially provided in the form of particles with sizes of between 0.5 nm and 1000 nm, preferably between 0.5 nm and 100 nm and more preferentially still between 1 and 20 nm.

The photocatalyst used in the process according to the invention can be provided in different forms or shapes (nanometric powder, nanoobjects comprising or not comprising cavities, films, monolith, beads of micrometric or millimetric size, and the like). The photocatalyst is advantageously provided in the form of a nanometric powder.

The Process for the Preparation of the Photocatalyst

The constituent semiconductor of said photocatalyst can be obtained by the preparation process as described below.

i) at least one source of tetravalent element, denoted X, at least one source of divalent metal, denoted Y, at least one source of sulfur, denoted S, at least one organic entity, denoted R, optionally at least one solvent, denoted SOLV, comprising at least one aqueous compound (denoted A) and/or at least one organic compound (denoted O), are mixed in order to obtain a precursor gel, said mixture exhibiting preferentially the following molar composition:

X/Y: at least 0.1, preferably from 1 to 200,
S/(X+Y): 0.05 to 50, preferably from 0.1 to 20,
R/(X+Y): 0.05 to 50, preferably from 0.1 to 20,
SOLV/(X+Y): 0 to 200, preferably from 1 to 100,
A/O: 0.005 to 100, preferably from 0.1 to 20, ii) a heat treatment of said precursor gel obtained on conclusion of stage i) is carried out at a temperature of between 120° C. and 250° C., for a period of time of between 2 days and 21 days.

The preparation process consists in preparing a reaction mixture, called gel, and including at least one source of tetravalent element, denoted X, one source of divalent metal, denoted Y, one source of sulfur, denoted S, at least one organic entity R, and optionally a solvent. The amounts of said reactants are adjusted so as to confer, on this gel, a composition making possible its crystallization to give a crystalline solid in its crude synthetic form of general formula $X_aY_bS_8$:cR, where a, b and c meet the criteria defined above.

Stage i)

The mixing stage i) is carried out until a homogeneous mixture is obtained, preferably for a period of time of greater than or equal to 15 minutes, preferably with stirring by any system known to a person skilled in the art, at a low or high shear rate. On conclusion of stage i), a homogeneous precursor gel is obtained.

It can be advantageous to add seeds to the reaction mixture during said stage i) of the process according to the invention in order to reduce the time necessary for the formation of the crystals and/or the total duration of crystallization. Said seeds also promote the formation of the crystalline solid to the detriment of impurities. Such seeds comprise crystalline solids, in particular solid crystals. The crystalline seeds are generally added in a proportion of between 0.01% and 10% by weight, with respect to the total weight of the tin and zinc precursors used in the reaction mixture.

It can be advantageous to carry out a maturing of the reaction mixture before the heat treatment during said stage i) of the process according to the invention, in order to control the size of the crystals of the crystalline solid. Said maturing also promotes the formation of said crystalline solid to the detriment of impurities. The maturing of the reaction mixture during said stage i) of the process according to the invention can be carried out at ambient temperature or at a temperature of between 20 and 100° C., with or without stirring, for a period of time advantageously of between 30 min and 48 hours.

When the photocatalyst comprises the solid IZM-5, said solid IZM-5 is obtained by reacting a mixture comprising at least one source of tin, denoted Sn, at least one source of zinc, denoted Zn, at least one source of sulfur, denoted S, at least one nitrogenous organic entity, denoted R, optionally at least one solvent, denoted SOLV, comprising at least one aqueous compound (denoted A) and/or at least one organic compound (denoted O), the mixture exhibiting preferentially the following molar composition:

Sn/Zn: at least 0.1, preferably at least 1, more preferably from 2 to 200,
S/(Sn+Zn): 0.1 to 20, preferably from 1 to 10,
R/(Sn+Zn): 0.1 to 10, preferably from 1 to 5,
SOLV/(Sn+Zn): 0 to 200, preferably 10 to 100, more preferably 20 to 100,
A/O: 0.01 to 10, preferably from 0.1 to 8, preferably from 0.2 to 5.

R is a nitrogenous organic entity having at least one nitrogen atom; preferably, R comprises two nitrogen atoms, acting as organic structuring. Preferably, R is the nitrogen compound 1,3-bis(4-piperidinyl)propane. Said nitrogenous organic entity used as structuring agent for the crystalline solid IZM-5 is synthesized by any method known to a person skilled in the art.

The source of tin, employed for carrying out the process for the preparation of the crystalline solid IZM-5, can be any compound which comprises the element tin and which can release this element into the mixture in reactive form. The source of tin is preferably tin acetate $Sn(CH_3CO_2)_4$, tin tert-butoxide $Sn(OC(CH_3)_3)_4$, tin tetrachloride $SnCl_4$, tin bis(acetylacetonate) dichloride $(CH_3COCH=C—(O—)CH_3)_2SnCl_2$, tin oxide $SnO_2$ or tin in metal form Sn.

The source of zinc, employed for carrying out the process for the preparation of the crystalline solid IZM-5, can be any compound which comprises the element zinc and which can release this element into the mixture in reactive form. The source of zinc is preferably zinc chloride $ZnCl_2$, zinc acetate Zn $(CH_3CO_2)_2$, zinc sulfate $ZnSO_4$, zinc nitrate $Zn(NO_3)_2$, zinc oxide ZnO or zinc in metal form Zn.

The source of sulfur, employed for carrying out the process for the preparation of the crystalline solid IZM-5, can be any compound which comprises the element sulfur and which can release this element into the mixture in reactive form. The source of sulfur is preferably solid or liquid under standard temperature and pressure conditions. The source of sulfur is preferably elemental sulfur S or $S_8$, sodium sulfide $Na_2S$, potassium sulfide $K_2S$, lithium sulfide $Li_2S$, ammonium sulfide $(NH_4)_2S$ or dimethyl disulfide $CH_3SSCH_3$.

The solvent, employed for the implementation of the process for the preparation of the crystalline solid IZM-5, can be an aqueous and/or organic compound. According to one alternative form, the solvent consists of an aqueous compound and of an organic compound. The aqueous compound is preferably chosen from water $H_2O$, and the organic compound is preferably chosen from compounds which are liquid under standard temperature and pressure conditions, of alcohol (preferably ethanol, isopropanol), diol (preferably ethylene glycol, propylene glycol), triol (preferably glycerol or propane-1,2,3-triol), organosulfur compound (preferably dimethyl sulfoxide or DMSO) or organonitrogen compound (preferably dimethylformamide or DMF) type.

According to another alternative form, no additional solvent is used in the process for the preparation of the crystalline solid IZM-5, and it is the nitrogenous organic entity, denoted R, when it is in liquid form under standard temperature and pressure conditions which makes possible the dissolution of the metal precursors and sulfur-based precursors.

Stage ii)

In accordance with stage ii) of the preparation process, the gel obtained on conclusion of stage i) is subjected to a heat treatment, preferentially carried out at a temperature of between 120° C. and 250° C. for a period of time of between 2 days and 21 days until the crystalline solid has formed.

The gel is advantageously placed under an autogenous reaction pressure, optionally while adding gas, for example nitrogen, at a temperature of between 120° C. and 250° C., preferably between 140° C. and 210° C., until crystals of solid in its crude synthesis form have formed.

The time necessary in order to obtain crystallization generally varies between 1 day and several months depending on the composition of the reactants in the gel, the stirring and the reaction temperature. Preferably, the crystallization time varies between 2 days and 21 days and preferably between 5 days and 15 days.

The reaction is generally carried out with stirring or in the absence of stirring, preferably with stirring. Use may be made, as stirring system, of any system known to a person skilled in the art, for example inclined blades with baffles, stirring turbomixers or Archimedean screws.

On conclusion of the heat treatment stage resulting in the crystallization of the solid, the solid phase is preferably filtered off, washed and then dried. Preferably, the washing stage will be carried out with ethanol or with the solvent used for the synthesis.

Advantageously, on conclusion of the heat treatment stage ii), optionally on conclusion of the filtering, washing and drying stages as described above, a stage of extraction of the organic entity R is carried out in order to release the microporosity by any method known to a person skilled in the art. Preferably, this stage can be carried out using heat treatment from 100° C. to 1000° C. under air, under oxygen, under hydrogen, under $H_2S$ or also under inert gas, such as $N_2$, alone or as a mixture. This extraction can also be carried out by ion exchange with entities such as $NH_4^+$, alkali metals, alkaline earth metals or any metal cation.

Stage b) of Irradiation of the Photocatalyst

According to stage b) of the process according to the invention, the photocatalyst is irradiated by at least one irradiation source producing at least one wavelength absorbable by the catalyst (i.e. lower than the bandgap width of the constituent semiconductor of said photocatalyst according to the alternative form where the photocatalyst is composed of at least one semiconductor) so as to reduce the carbon dioxide and to oxidize the sacrificial compound in the presence of said photocatalyst activated by said irradiation source, so as to produce an effluent containing, at least in part, $C_1$ or more carbon-based molecules other than $CO_2$.

A photocatalyst comprising one or more semiconductors based on microporous crystalline metal sulfide can be activated by the absorption of at least one photon.

Absorbable photons are those, the energy of which is greater than the bandgap width. In other words, the photocatalysts can be activated by at least one photon with a wavelength corresponding to the energy associated with the bandgap widths of the semiconductors constituting the photocatalyst or with a lower wavelength.

Any irradiation source emitting at least one wavelength suitable for the activation of said photocatalyst, that is to say absorbable by the photocatalyst, can be used according to the invention. The irradiation source can just as well be natural, by solar irradiation, as artificial, of laser, Hg, incandescent lamp, fluorescent tube, plasma or light-emitting diode (LED) type. In a preferred way, the irradiation source is natural, preferably by solar irradiation.

The irradiation source produces radiation, at least a portion of the wavelengths of which are lower than the maximum wavelength (λmax) absorbable by the constituent semiconductors of the photocatalyst according to the invention. When the irradiation source is solar irradiation, it generally emits in the ultraviolet, visible and infrared spectrum, that is to say it emits a wavelength range from 280 nm to 2500 nm approximately (according to the standard ASTM G173-03). Preferably, the source emits at at least one wavelength range greater than 280 nm, very preferably of between 315 nm to 800 nm, which includes the UV spectrum and/or the visible spectrum.

The irradiation source provides a stream of photons which irradiates the reaction medium containing the photocatalyst. The interface between the reaction medium and the light source varies according to the applications and the nature of the light source.

When the irradiation source is natural, for example solar irradiation, the irradiation source is located outside the reactor and the interface between the two can be an optical window made of pyrex, of quartz or of organic glass or any other interface making it possible for the photons absorbable by the photocatalyst according to the invention to diffuse from the external environment within the reactor.

The implementation of the photocatalytic reduction of carbon dioxide is conditioned by the supply of suitable photons to the photocatalytic system for the envisaged reaction and for this reason is not limited to specific pressure or temperature ranges apart from those making it possible to ensure the stability of the product(s). The temperature range employed for the photocatalytic reduction of the charge containing the carbon dioxide is generally from −10° C. to +200° C., preferably from 0 to 150° C. and very preferably from 0 to 50° C. The pressure range employed for the photocatalytic reduction of the charge containing the carbon dioxide is generally from 0.01 MPa to 70 MPa (0.1 to 700 bar), preferably from 0.1 MPa to 5 MPa (1 to 50 bar).

A diluent fluid, such as described in stage a), can be present in the reaction medium when the process is carried out in the gas phase, during the irradiation.

The effluent obtained after the reaction for the photocatalytic reduction of carbon dioxide contains, on the one hand, at least one $C_1$ or more molecule other than carbon dioxide resulting from the reaction and, on the other hand, unreacted charge, and also the optional diluent fluid, but also parallel reaction products, such as molecular hydrogen resulting from the photocatalytic reduction of $H_2O$ when this compound is used as sacrificial compound.

The following examples illustrate the invention without limiting the scope thereof.

EXAMPLES

Example 1: Photocatalyst A—$TiO_2$

The photocatalyst A is a semiconductor based on commercial $TiO_2$ (Aeroxide® P25, Aldrich™, purity >99.5%). The particle size of the photocatalyst, measured by transmission electron microscopy (TEM), is 21 nm and the specific surface, measured by the BET method, is equal to 52 $m^2/g$.

The photocatalyst A has a bandgap width of 3.1 eV, measured by UV-visible diffuse reflectance spectrometry, and does not exhibit microporosity.

Example 2: Preparation of a Solid IZM-5

0.228 g of tin dioxide ($SnO_2$, purity 99% by weight, Sigma-Aldrich) was mixed with 0.146 g of zinc nitrate ($Zn(NO_3)_2 \cdot 6H_2O$, purity 99% by weight, Alfa Aesar). Subsequently, 0.277 g of sulfur (S, purity 99.98% by weight, Aldrich) and 2.001 g of 1,3-bis(4-piperidyl)propane (compound R, purity 97% by weight, Aldrich) are added to the preceding mixture. Finally, 11.2 ml of ethylene glycol (purity 99.8% by weight, VWR) and 3.7 ml of deionized water are incorporated and the synthesis gel is kept stirring (250 rpm) for 30 minutes. The precursor gel is subsequently transferred, after homogenization, into an autoclave. The autoclave is closed and then heated at 190° C. for 12 days under static conditions. The crystalline product obtained is filtered, washed with ethanol and then dried overnight at 100° C. The crude solid synthesis product was analyzed by X-ray diffraction and identified as being formed of solid IZM-5. The product exhibits an Sn/Zn molar ratio of 5.7, as determined by ICP-MS. The elemental analysis gives the following molar composition: $Sn_{3.4}Zn_{0.6}S_8:1.1R$.

Example 3: Photocatalyst B

The solid obtained in example 2 is subjected to a heat treatment in order to extract all or part of the compound R in order to release the microporosity. A mixture comprising 50% by volume of $N_2$ and 50% by volume of air, at a flow rate of 2 Sl/h/g, is introduced into a reactor of crossed bed type containing the solid IZM-5 obtained in example 2. The temperature is increased to 120° C. at a rate of 1° C./min, then left for 1 h. In a second step, the temperature is increased to 300° C. at a rate of 1° C./min, then left for 2 h. Finally, the temperature is allowed to fall again to ambient temperature by the inertia of the reactor.

The solid recovered is called photocatalyst B. The photocatalyst B has a bandgap width of 2.6 eV, measured by UV-visible diffuse reflectance spectrometry, and exhibits a micropore volume of 0.1 ml/g.

Example 4: Employment of the Photocatalysts A and B in Photocatalytic Reduction of $CO_2$ in the Gas Phase The solids A and B are subjected to a test of photocatalytic reduction of $CO_2$ in the gas phase in a continuous crossed bed reactor made of steel and fitted with an optical window made of quartz with a surface area of $5.3 \times 10^{-4}$ $m^2$ and with a sintered glass facing the optical window on which the photocatalytic solid is deposited.

About 100 mg of photocatalyst are deposited on the sintered glass. The tests are carried out at ambient temperature under atmospheric pressure. A flow of $CO_2$ of 18 ml/h passes through a water saturator before being distributed in the reactor. The production of $CH_4$ and CO resulting from the reduction of carbon dioxide is monitored by an analysis of the effluent every 6 minutes by micro gas chromatography. The UV-visible irradiation source is provided by an Xe—Hg lamp (Asahi™, MAX302™). The irradiation power is always maintained at 130 $W/m^2$, measured for a wavelength range of between 315 nm and 400 nm. The duration of the test is 20 hours.

The comparison of the mean photocatalytic activities is expressed in μmol of methane or of carbon monoxide produced per hour and per irradiation surface area. The results are given in table 2 below. The activity values show that the use of the solids according to the invention exhibits the best photocatalytic performance qualities.

| Photocatalyst | Production of CH$_4$ (μmol/h/m$^2$) | Production of CO (μmol/h/m$^2$) |
|---|---|---|
| A (comparative) | 1.0 | 1.3 |
| B (according to the invention) | 40 | 110 |

The invention claimed is:

1. A process for the photocatalytic reduction of carbon dioxide carried out in the liquid phase and/or in the gas phase, said process comprising:
   a) bringing a charge containing carbon dioxide and at least one sacrificial compound into contact with a photocatalyst comprising at least one semiconductor based on microporous crystalline metal sulfide; and
   b) irradiating the photocatalyst by at least one irradiation source producing at least one wavelength which is lower than the bandgap width of said photocatalyst, said irradiating being carried out at a temperature of between −10° C. and 200° C. and at a pressure of between 0.01 MPa and 70 MPa;
   wherein said photocatalyst is provided in the form of a solid comprising a chemical composition expressed on an anhydrous basis, in terms of moles, by the following formula:

$X_aY_bS_8$:cR where:
   X represents at least one tetravalent element selected from Sn, Ge, Ti, and Zr,
   Y represents at least one divalent metal selected from Zn, Cd, and Ni,
   R represents at least one nitrogenous organic entity,
   S is sulfur,
   "a" is the molar amount of X and is between 0.1 and 5;
   "b" is the molar amount of Y and is between 0.2 and 8;
   "c" is the molar amount of the nitrogenous organic entity R and is between 0 and 4.

2. The process as claimed in claim 1, wherein said photocatalyst is provided in the form of a solid comprising a chemical composition expressed on an anhydrous basis, in terms of moles, defined by the following general formula:

$Sn_aZn_bS_8$:cR where:
   R represents at least one nitrogenous organic entity;
   S is sulfur;
   "a" is the molar amount of Sn and is between 0.1 and 5;
   "b" is the molar amount of Zn and is between 0.2 and 8;
   "c" is the molar amount of the nitrogenous organic entity R and is between 0 and 4.

3. The process as claimed in claim 1, in which "c" is between 0.2 and 4.

4. The process as claimed in claim 3, in which said solid exhibits an X-ray diffraction diagram including at least the lines listed in the table below:

| 2 theta (°) | d$_{hkl}$ (Å) | l$_{rel}$ |
|---|---|---|
| 7.95 | 11.11 | S |
| 8.88 | 9.95 | m |
| 10.18 | 8.68 | w |
| 11.10 | 7.97 | VS |
| 11.72 | 7.54 | S |
| 15.37 | 5.76 | m |
| 16.71 | 5.30 | w |
| 17.36 | 5.11 | w |
| 21.49 | 4.13 | m |
| 22.30 | 3.98 | m |
| 23.31 | 3.81 | w |
| 30.05 | 2.97 | w |
| 33.34 | 2.69 | w |
| 35.96 | 2.50 | w |
| 40.80 | 2.21 | w | where VS = very strong; S = strong; m = medium; w = weak.

5. The process as claimed in claim 1, in which R is an organic compound comprising at least two nitrogen atoms.

6. The process as claimed in claim 5, in which R is 1,3-bis(4-piperidinyl)propane.

7. The process as claimed in claim 1, in which said semiconductor exhibits a micropore volume of between 0.01 and 0.50 cm$^3$/g.

8. The process as claimed in claim 1, in which the width of the bandgap of said photocatalyst is between 1.24 and 3 eV.

9. The process as claimed in claim 1, in which, when said process is carried out in the gas phase, the sacrificial compound is a gaseous compound selected from water, ammonia, hydrogen, methane, an alcohol, and mixtures thereof.

10. The process as claimed in claim 1, in which, when the process is carried out in the liquid phase, the sacrificial compound is a soluble solid or liquid compound selected from water, ammonia, an alcohol, an aldehyde, and an amine.

11. The process as claimed in claim 1, in which the irradiation source is a natural irradiation source.

12. The process as claimed in claim 1, in which the irradiation source emits at at least one wavelength range greater than 280 nm.

13. The process as claimed in claim 12, in which the irradiation source emits at at least one wavelength range of between 315 nm and 800 nm.

14. The process as claimed in claim 9, wherein the sacrificial compound is a gaseous compound selected from water and hydrogen.

15. The process as claimed in claim 10, wherein the sacrificial compound is water.

16. The process as claimed in claim 1, in which said semiconductor exhibits a micropore volume of between 0.05 and 0.30 cm$^3$/g.

* * * * *